United States Patent [19]
Dietz et al.

[11] Patent Number: 5,338,490
[45] Date of Patent: Aug. 16, 1994

[54] TWO-PHASE COMPOSITES OF IONICALLY-CONDUCTIVE PRESSURE-SENSITIVE ADHESIVE, BIOMEDICAL ELECTRODES USING THE COMPOSITES, AND METHODS OF PREPARING THE COMPOSITE AND THE BIOMEDICAL ELECTRODES

[75] Inventors: Timothy M. Dietz, St. Paul, Minn.; Robert A. Asmus, Hudson, Wis.; Rosa Uy, St. Paul, Minn.

[73] Assignee: Minnesota Mining and Manufacturing Company, St. Paul, Minn.

[21] Appl. No.: 114,971

[22] Filed: Aug. 31, 1993

Related U.S. Application Data

[63] Continuation of Ser. No. 792,374, Nov. 15, 1991, abandoned.

[51] Int. Cl.⁵ .......................... A61F 13/02; C08J 3/00; C08K 5/15; C08L 5/00
[52] U.S. Cl. .................................... 252/500; 525/205; 525/195; 525/57; 524/394; 524/401; 524/56; 524/516; 424/448
[58] Field of Search ................. 252/500; 525/205, 195, 525/57; 524/394, 401, 56, 516; 424/448

[56] References Cited

U.S. PATENT DOCUMENTS

| | | | |
|---|---|---|---|
| Re. 24,906 | 12/1960 | Ulrich | 526/318.2 |
| 3,998,215 | 12/1976 | Anderson et al. | 128/2.06 |
| 4,273,135 | 6/1981 | Larimore et al. | 128/640 |
| 4,300,820 | 11/1981 | Shah | 351/160 |
| 4,307,717 | 12/1981 | Hymes et al. | 128/156 |
| 4,337,325 | 6/1982 | Shah | 525/205 |
| 4,352,359 | 10/1982 | Larimore et al. | 128/640 |
| 4,356,819 | 11/1982 | Potaczek | 128/156 |
| 4,367,732 | 1/1983 | Poulen et al. | 128/150 |
| 4,369,229 | 1/1983 | Shah | 428/421 |
| 4,524,087 | 6/1985 | Engel | 427/2 |
| 4,539,996 | 9/1985 | Engel | 128/640 |
| 4,554,924 | 11/1985 | Engel | 128/640 |
| 4,588,762 | 5/1986 | Mruk et al. | 524/45 |
| 4,593,053 | 6/1986 | Jevne et al. | 523/111 |
| 4,693,887 | 9/1987 | Shah | 424/19 |
| 4,699,146 | 10/1987 | Sieverding | 128/640 |
| 4,715,382 | 12/1987 | Strand | 128/640 |
| 4,750,482 | 6/1988 | Sieverding | 128/156 |
| 4,771,783 | 9/1988 | Roberts | 128/640 |
| 4,795,516 | 1/1989 | Strand | 156/235 |
| 4,798,642 | 1/1989 | Craighead et al. | 156/252 |
| 4,810,418 | 3/1989 | Burvee | 252/500 |
| 4,830,776 | 5/1989 | Thompson | 252/500 |
| 4,846,185 | 7/1989 | Carim | 128/641 |
| 4,848,353 | 7/1989 | Engel | 128/640 |
| 4,943,461 | 7/1990 | Karim | 428/40 |
| 4,985,488 | 1/1981 | Landin | 524/555 |
| 4,994,322 | 2/1991 | Delgado et al. | 428/343 |
| 5,012,810 | 5/1991 | Strand et al. | 128/640 |
| 5,024,227 | 6/1991 | Schmid | 128/640 |
| 5,270,358 | 12/1993 | Asmus | 524/55 |
| 5,276,079 | 1/1994 | Duan et al. | 524/386 |

FOREIGN PATENT DOCUMENTS

| | | |
|---|---|---|
| 0058485 | 8/1982 | European Pat. Off. ........ A61N 1/30 |
| 0066887 | 12/1982 | European Pat. Off. . |
| 0308572 | 3/1989 | European Pat. Off. ........ A61N 1/30 |
| 0322098 | 6/1989 | European Pat. Off. ..... C08F 226/06 |
| WO89/00771 | 1/1989 | PCT Int'l Appl. ........... H01M 6/18 |
| WO90/11719 | 10/1990 | PCT Int'l Appl. ............ A61B 5/04 |
| WO91/09633 | 7/1991 | PCT Int'l Appl. ........... A61L 15/22 |
| 2008000 | 5/1979 | United Kingdom . |

OTHER PUBLICATIONS

Errede, "Molecular Interpretations of Sorption in Polymers Part I", *Advances in Polymer Science*, vol. 99, Springer-Verlag, Berlin Heidelberg Germany (pp. 22–36, 1991).

*Primary Examiner*—Linda Skaling
*Assistant Examiner*—Michael P. Tierney
*Attorney, Agent, or Firm*—Gary L. Griswold; Walter N. Kirn; John H. Hornickel

[57] ABSTRACT

A two-phase composite of ionically-conductive pressure-sensitive adhesive, biomedical electrodes using the composite and methods of preparing the composite and the electrode are disclosed. The continuous phase is a hydrophilic, solid state pressure-sensitive adhesive composition ionically-conductive regardless of an amount of water present in the composition. The discontinuous phase are domains of a hydrophobic pressure-sensitive adhesive which enhances adhesion of the composite to mammalian skin while maintaining acceptable alternating current impedance of the composite.

30 Claims, 1 Drawing Sheet

TWO-PHASE COMPOSITES OF IONICALLY-CONDUCTIVE PRESSURE-SENSITIVE ADHESIVE, BIOMEDICAL ELECTRODES USING THE COMPOSITES, AND METHODS OF PREPARING THE COMPOSITE AND THE BIOMEDICAL ELECTRODES

This is a continuation of application Ser. No. 07/792,374 filed Nov. 15, 1991, now abandoned.

FIELD OF THE INVENTION

This invention relates to composites of a continuous phase of an ionically-conductive, hydrophilic, solid state, pressure-sensitive adhesive having domains of hydrophobic, pressure-sensitive adhesive dispersed therein. This invention also relates to biomedical electrodes using such composites as a ionically-conductive medium, and methods of preparing such composites and electrodes.

BACKGROUND OF THE INVENTION

Modern medicine uses many medical procedures where electrical signals or currents are received from or delivered to a patient's body. The interface between medical equipment used in these procedures and the skin of the patient is usually some sort of biomedical electrode. Such an electrode typically includes a conductor which must be connected electrically to the equipment, and a conductive medium adhered to or otherwise contacting skin of a patient.

Among the therapeutic procedures using biomedical electrodes are transcutaneous electronic nerve stimulation (TENS) devices used for pain management; neuromuscular stimulation (NMS) used for treating conditions such as scoliosis; defibrillation electrodes to dispense electrical energy to a chest cavity of a mammalian patient to defibrillate heart beats of the patient; and dispersive electrodes to receive electrical energy dispensed into an incision made during electrosurgery.

Among diagnostic procedures using biomedical electrodes are monitors of electrical output from body functions, such as electrocardiogram (ECG) for monitoring heart activity and for diagnosing heart abnormalities.

For each diagnostic, therapeutic, or electrosurgical procedure, at least one biomedical electrode having an ionically conductive medium containing an electrolyte is adhered to or otherwise contacting mammalian skin at a location of interest and also electrically connected to electrical diagnostic, therapeutic, or electrosurgical equipment. A critical component of the biomedical electrode is the conductive medium serving as the interface between mammalian skin and diagnostic, therapeutic, or electrosurgical equipment.

Biomedical electrodes are used among other purposes to monitor and diagnose a patient's cardiovascular activity. Diagnostic electrodes are used to monitor the patient immediately and are only applied to the patient for about five to ten minutes. Monitoring electrodes are used on patients in intensive care for up to three days continuously. Holter electrodes are used to monitor a patient during strenuous and daily activities.

All of these biomedical electrodes are used to record cardiovascular activity although each electrode requires specific features to be successful. The diagnostic electrode does not have to remain adhered to a patient for extensive periods but does have to adhere to hairy, oily, dry and wet skin effectvely for the five to ten minutes of use. The monitoring electrode has to adhere for a longer period of time although the patient is often immobile during the monitoring period. The Holter electrode is susceptible to disruption from adhesion due to physical motion, perspiration, water, etc., and therefore requires the best adhesion and at the same time comfort and electrical performance.

The ionically conductive medium which serves as an interface between the skin of a mammalian patient and the electrical instrumentation ranges from conductive gels and creams to conductive pressure sensitive adhesives. However, while conductive media can be pressure sensitive adhesives, for monitoring or Holter biomedical electrode use, such conductive adhesives are not adequate alone to maintain adhesion to mammalian skin. Hypoallergenic, hydrophobic pressure sensitive adhesives are employed around the conductive medium to provide the required mammalian skin adhesion. U.S. Pat. No. 5,012,810 (Strand et al.) and U.S. Pat. Nos. 4,527,087; 4,539,996; 4,554,924; and 4,848,353 (all Engel) disclose biomedical electrodes which have a hydrophobic pressure sensitive adhesive surrounding the conductive medium.

Conductive media are typically hydrophilic and need water or an aqueous ionic system to provide required ionic conductivity between mammalian skin and electrical diagnostic, therapeutic, or electrosurgical instrumentation. Hydrophilic pressure sensitive adhesives generally have less skin adhesion than hydrophobic adhesives. Sometimes, such hydrophilic pressure-sensitive adhesives can not function as adhesives to mammalian skin for the period of time necessary to complete a medical procedure.

To improve the tack of conductive hydrogels, tackifiers have been added. U.S. Pat. No. 4,593,053 (Jevne et al.) discloses the addition of poly-2-acrylamido-2-methyl propane sulfonic acid, its salts, polyacrylic acid, polystyrene sulfonic acid or salts thereof, karaya, xanthan, guar, or locust bean gums in an amount of 2 to 20 weight percent to increase tackiness of gel containing polyvinylpyrrolidone and polyvinyl alcohol.

Also, adhesive additives have been used in the formation of the solid phase of a matrix useful as a medical bandage. U.S. Pat. No. 4,307,717 (Hymes et al.) discloses the addition of vinyl acetate dioctyl maleate copolymer to intensify the tackiness of the bandage.

Rather than employ a single phase hydrogel for the conductive medium, U.S. Pat. No. 4,588,762 (Mruk et al.) discloses a heterogeneous, pressure-sensitive, electrically conductive adhesive for disposable biomedical electrodes consisting of a viscoelastic polymeric adhesive phase and an electrically conductive aqueous phase containing a water receptive polymer, humectant, and an electrolyte. Both phases are intimately interdispersed and the adhesive is applied as a relatively thin film on a supporting substrate. The final film constitutes a heterogeneous system in which the aqueous zones or islands defined by the water receptive polymer extend through the thickness of the film and are distributed throughout the expanse of a continuous matrix consisting of the adhesive polymer. However, to be electrically conductive, such zones or islands must contact both mammalian skin and electrically conductive materials in the biomedical electrode. If such zones or islands do not transverse the thickness of the film, they are electrical dead ends.

PCT International Publication WO 91/09633 (Asmus) discloses a two-phase composite of a continuous phase of a pressure sensitive adhesive matrix having dispersed therein swollen, discrete gel particles. If such particles were ionically conductive, such particles could not transmit electrical signals between mammalian skin and electrical instrumentation unless such particles transversed the thickness of the continuous phase.

SUMMARY OF THE INVENTION

The present invention solves the problem in the art of improving mammalian skin adhesion for ionically-conductive, hydrophilic, solid state, pressure-sensitive adhesives useful in biomedical electrodes without affecting adversely the ionic-conductivity of the pressure-sensitive adhesive.

Adhesives of the present invention do not rely on the electrical conductivity of aqueous zones or gel particles in a continuous pressure-sensitive adhesive phase to transverse the thickness of the phase. Nor do adhesives of the present invention require a hydrophobic pressure sensitive adhesive to impart adhesiveness.

The present invention provides a ionically-conductive, pressure-sensitive adhesive which can function on mammalian skin over a longer period of contact without loss of pressure-sensitive properties than hydrophilic pressure-sensitive adhesives previously known.

The present invention comprises a two-phase composite of ionically-conductive, pressure-sensitive adhesive. The ionically-conductive, pressure-sensitive adhesive comprises a continuous phase of hydrophilic, solid state pressure-sensitive adhesive composition ionically-conductive regardless of an amount of water present in the composition, and a discontinous phase of domains of hydrophobic, pressure-sensitive adhesive composition present in the continuous phase in an amount to enhance pressure-sensitive adhesive properties for contacting mammalian skin while maintaining acceptable alternating current impedance.

The present invention achieves the purposes of a hydrophilic, ionically-conductive medium for a biomedical electrode with the advantages of improved mammalian skin adhesion but without loss of electrical properties.

The present invention provides an advantage that a two-phase composite can be applied or coated on conductor members of biomedical electrodes in a thickness about four times thinner than thickness of a conventional hydrophilic pressure sensitive adhesive in a biomedical electrode. This results in a lower profile biomedical electrode suitable for more flexible and versatile uses.

The present invention also provides the advantage of employing the benefits of both phases of the two-phase composite of the present invention: ionic conductivity and moisture absorption provided by the continuous phase and hypoallergenic, enhanced adhesion provided by the discontinuous phase.

The present invention also provides the advantage of adjusting the mammalian skin adhesion of the two-phase composite by controlling the amount of hydrophobic pressure sensitive adhesive particles dispersed in the continuous, hydrophilic, solid state, pressure-sensitive adhesive.

The present invention also comprises a biomedical electrode comprising a conductive medium of a two-phase composite of the present invention and means for electrical communication interacting between the conductive medium and electrical diagnostic, therapeutic, or electrosurgical equipment.

The present invention also comprises a method of preparing a two-phase composite of the present invention, comprising the steps of: (a) mixing solvating polymer, ionic salt, and an amount of essentially non-volatile plasticizer sufficient to form a cohesive, hydrophilic solid state pressure-sensitive adhesive, into a solvent which is essentially volatile above ambient temperatures to form a first suspension or solution; (b) mixing a latex or solution of hydrophobic pressure-sensitive adhesive into the first suspension or solution in a weight ratio of from about 196:1 to about 6:1 of first suspension or solution:latex or solution to form a combined mixture; (c) casting the combined mixture onto a substrate; and (d) removing the solvent to form a two-phase composite. When the substrate on which the combined mixture is cast has an electrically conductive surface, a biomedical electrode is formed.

Embodiments of the invention are described in relation to the Drawing.

EMBODIMENTS OF THE INVENTION

Figure 1:
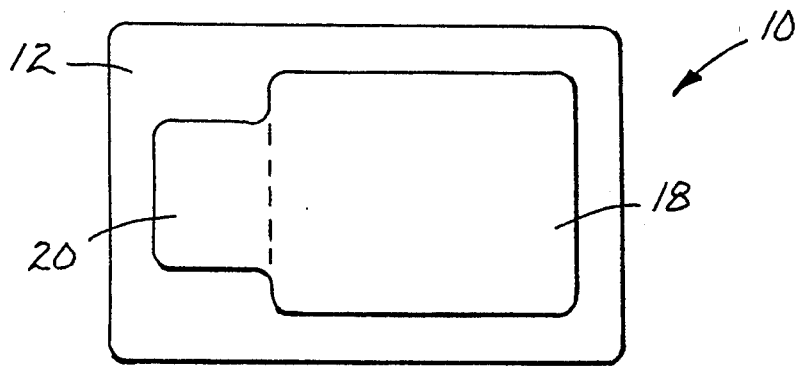
FIG. 1 is a top plan view of a biomedical electrode containing a two-phase composite of the present invention as the conductive medium.

Continuous Phase of Ionically-Conductive, Hydrophilic, Solid State, Pressure-Sensitive Adhesive The continuous phase is a solid state conductive pressure-sensitive adhesive composition which is ionically-conductive regardless of the amount of water present during manufacture, storage or use. Solid state conductive pressure-sensitive adhesive compositions are disclosed in copending, coassigned U.S. patent application Ser. No. 07/792,957 (Attorney Docket Number 47073USA6A), the disclosure of which is incorporated by reference. Such pressure-sensitive adhesives are not susceptible to a loss of conductivity due to dehydration of water or other volatile components after manufacture and prior to completion of use. Nor is the conductivity of such adhesives impaired by the absorption of water into such adhesives in humid atmospheric conditions.

Solid state pressure-sensitive adhesives can be made with minimal amounts of water present during manufacture. Such adhesives can be stored in humid or arid conditions without protection from atmospheric moisture. Such adhesives can be used without regard to the amount of atmospheric moisture or body fluids or exudate likely to be encountered during diagnostic, therapeutic, or electrosurgical procedures. In short, these pressure-sensitive adhesives solve the problem of requiring water to achieve ionical conductivity in conductive media in biomedical electrodes which contact mammalian skin. Solid state conductive pressure-sensitive adhesive compositions function independently of the presence or absence of water. Water is accommodated in such adhesives, but not required for use.

A solid state conductive pressure-sensitive adhesive composition, ionically-conductive regardless of an amount of water present in the composition, comprises a polymer electrolyte complex and an essentially nonvolatile plasticizer in an amount sufficient to form a cohesive, pliable, pressure-sensitive adhesive.

A polymer electrolyte complex comprises a solid solution of ionic salt dissolved in a solvating polymer. A conductive solid solution is achieved through dissociation of ionic salts by a solvating polymer, forming a cation-polymer complex and its counterion. The cation-polymer complex occurs with direct interaction of non-carbon atoms in the polymer chain.

A solvating polymer can be either a homopolymer where each monomeric unit has at least one ionizing non-carbon atom or a copolymer where at least one monomeric unit has at least one ionizing non-carbon atom contained in a pendant group to the monomeric unit. Nonlimiting examples of a non-carbon atom in a monomeric unit include oxygen, nitrogen, sulphur, and phosphorus.

Solvating polymer is present in a solid state conductive pressure-sensitive adhesive in an amount from about 5 to 50 weight percent, and preferably from about 20 to about 45 weight percent, of the adhesive.

Of possible solvating polymers, crosslinked poly(N-vinyl lactam); crosslinked polyacrylamide or its ionic forms; crosslinked polyacrylic acid or its salts; crosslinked poly(2-acrylamide-2-methylpropanesulfonic acid), its salts, crosslinked copolymers of the acid, crosslinked copolymers of salts of the acid, or mixtures thereof; or combinations of these solvating polymers are preferred. Of these preferred solvating polymers, a crosslinked poly(N-vinyl lactam) is especially preferred.

Crosslinked poly(N-vinyl lactam) can be crosslinked from either a noncrosslinked homopolymer or a noncrosslinked copolymer containing N-vinyl lactam monomeric units. Such crosslinked poly(N-vinyl lactam) is swellable in a plasticizer biocompatible with mammalian skin.

Preferably, noncrosslinked homopolymer or noncrosslinked copolymer is soluble in plasticizer biocompatible with mammalian skin in the absence of radiation crosslinking. Preferably, N-vinyl lactam monomeric units comprise a majority of total monomeric units of the polymer.

Nonlimiting examples of N-vinyl lactam monomers are N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone. Preferably, the poly(N-vinyl lactam) is a homopolymer of N-vinyl-2-pyrrolidone.

Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

The N-vinyl lactam monomeric units comprise no less than about 50 weight percent of the monomeric units present in the poly(N-vinyl lactam) in solid state form. More preferably, the N-vinyl lactam monomeric units comprise 70 to 100 percent by weight of the poly(N-vinyl lactam) and most preferably 90 to 100 percent by weight of the poly(N-vinyl lactam).

Noncrosslinked poly(N-vinyl lactam) homopolymer and poly(N-vinyl pyrrolidone)/poly vinyl acetate copolymers are commercially available. Nonlimiting examples of commercially available poly(N-vinyl pyrrolidone) useful for the present invention include Aldrich Chemical Co. of Wilwaukee, Wis., BASF of Parsippany, N.J., and ISP (GAF) of Wayne, N.J.

Poly(N-vinyl lactam) can have a Fikentscher K-value of at least K-15 and preferably at least K-60, and most preferably at least K-90. Fikentscher K-values are described in Molyneaux, Water-Soluble Polymers: Properties and Behavior, Vol. 1, CRC Press, 1983, pp. 151–152.

After exposure to ionizing radiation, poly(N-vinyl lactam) can have a Swelling Capacity, S, milliliters of liquid sorbed per gram of polymer, of at least about 15 in water, preferably about 20–35 in water, and most preferably about 25 in water.

Swelling Capacity correlates to a measurement of polymer swelling as a function of chemical crosslinking units in poly(N-vinyl lactam), according to the equation:

$$S = C(\lambda^{\frac{1}{2}} - \lambda_0^{\frac{1}{2}})$$

where S is a measurement of water sorbed per gram of polymer, C is a constant characteristic of the polymer, i.e., milliliters of water sorbed per gram of polymer, $\lambda$ is the average number of backbone carbon atoms in the polymer segments between crosslinked junctions, and $\lambda_0$ is the average number of backbone carbon atoms in the polymer segments between crosslinked junctions when S is zero. Swelling capacity and this equation are discussed in Errede, "Molecular Interpretations of Sorption in Polymers Part I", *Advances in Polymer Science* Vol. 99, Springer-Verlag, Berlin Heidelberg Germany (pp. 21–36, 1991), the disclosure of which is incorporated by reference.

Poly(N-vinyl lactam) useful in the present invention can be in any form susceptible to being crosslinked, but preferably is in a solid state form. Nonlimiting examples of solid state forms include particles, pellets, sheets, strands, fibers, membranes, films, and other three dimensional functional forms. Preferably, poly(N-vinyl lactam) is in the form of particles of a size from about 0.1 micrometers to about 250 micrometers and preferably from about 10 micrometers to about 75 micrometers.

Poly(N-vinyl lactam) can be crosslinked using bulk polymerization in the presence of a chemical crosslinking agent, solution polymerization in the presence of a chemical crosslinking agent, thermal polymerization in the presence of a chemical crosslinking agent, or photo-initiated polymerization in the presence of a chemical crosslinking agent. Preferred crosslinked polymerization methods include free-radical polymerization methods employing chemical crosslinking agents such as that disclosed in U.S. Pat. No. 4,848,353 (Engel) or EPO Publication 0 322 098 (Duan). Poly(N-vinyl lactam) can also be crosslinked using ionizing radiation such as that disclosed in copending, co-assigned U.S. patent application Ser. No. 07/792,442 (Docket No. 45911USA1A), the disclosures of such methods of crosslinking being incorporated by reference as if rewritten herein.

Crosslinked polyacrylamide or its ionic forms; crosslinked polyacrylic acid or its salts; crosslinked poly(2-acrylamide-2-methylpropanesulfonic acid), its salts, crosslinked copolymers of the acid, crosslinked copolymers of salts of the acid, or mixtures thereof; or combinations of these crosslinked solvating polymers can be prepared by using free-radical polymerization methods known to those skilled in the art.

To render a solvating polymer pressure-sensitive adhesive, the plasticizer can be an essentially non-volatile liquid or combination of liquids which can swell the solvating polymer and which is biocompatible with mammalian skin.

Essentially non-volatile means that a plasticizer as used in the present invention will render a polymer electrolyte complex of solvating polymer and ionic salt sufficiently cohesive and pliable such that less than ten percent (10%) of a given volume of plasticizer evaporates after exposure to a temperature of processing the composition or to a temperature of storage conditions.

Non-limiting examples of essentially non-volatile plasticizers include polyhydric alcohols (e.g., ethylene glycol, propylene glycol, sorbitol, polyethylene glycol (200–600 M.W.), and glycerin) and other plasticizers which are non-volatile in ambient conditions and do not cause mammalian skin irritation or toxic reaction.

Essentially non-volatile plasticizer can be added in an amount sufficient to form a cohesive and pliable pressure-sensitive adhesive. The amount of plasticizer to be added depends on the type of solvating polymer employed and the extent of crosslinking in the polymer. To achieve a pressure-sensitive adhesive, the essentially non-volatile plasticizer can be added to solvating polymer ranging from about 50 to about 95 weight percent of the solid state conductive pressure-sensitive adhesive composition. When the solvating polymer is crosslinked poly(N-vinyl lactam), the amount of plasticizer can range from about 50 to 75 weight percent of the composition. The amount of plasticizer can range from 65 to about 95 weight percent when the solvating polymer is crosslinked polyacrylic acid; crosslinked polyacrylamide; or poly(2-acrylamido-2-methyl sulfonic acid), its salts, copolymers of the acid, copolymers of the salt, or mixtures thereof. Within these ranges, one can adjust the amount of plasticizer employed to control adhesive properties of the polymer electrolyte complex.

Of essentially non-volatile plasticizers, glycerin and polyethylene glycol are preferred, with polyethylene glycol most preferred. Glycerin and polyethylene glycol can be used in mixtures. Glycerin can comprise up to 100 weight percent of the essentially non-volatile plasticizer. Preferably, polyethylene glycol can comprise up to 100 weight percent of the essentially non-volatile plasticizer. Polyethylene glycol of either 300 molecular weight or 400 molecular weight is preferred, with 300 molecular weight more preferred.

Unexpectedly, solid state conductive pressure-sensitive adhesive compositions do not require the use of water, or the retention of water or any other volatile liquid capable of vaporization at ambient conditions, as a plasticizer for polymer electrolyte complex to provide ionic conductivity. By relying on essentially non-volatile plasticizers to form cohesive, pliable solid state conductive pressure-sensitive adhesives, biomedical electrodes employing such solid state conductive pressure-sensitive adhesives are less apt to have ionic conductivity altered by dehydration of a component of the composition.

While solid state conductive pressure-sensitive adhesive compositions do not require water to be present, such compositions can accommodate the presence of water in such composition without losing ionic conductivity or adhesive performance. Thus, solid state conductive pressure-sensitive adhesive compositions function regardless of the amount of water present during manufacture, storage, or use.

Solvating polymers contain one or more ionic salts in amounts sufficient to interact with non-carbon atoms of the solvating polymer in order to form polymer electrolyte complexes which can be plasticized to form solid state conductive pressure-sensitive adhesive compositions. In effect, solid state conductive pressure-sensitive adhesive composition is a matrix of (a) a conductive solid solution of one or more ionic salts dissociating in a solvating polymer and (b) an essentially non-volatile plasticizer present, if any, in an amount sufficient to render the matrix cohesive and pliable, and preferably pressure-sensitive adhesive. Thus, unexpectedly, the interaction of ionic salts with the solvating polymer provides ionic conductivity for the composition. Ionic or polar solvents such as water previously employed in polyelectrolyte compositions are not necessary to provide ionic conductivity in a conductive medium of a biomedical electrode.

Non-limiting examples of ionic salts useful for interaction with the solvating polymer include lithium chloride, lithium perchlorate, sodium citrate, and preferably potassium chloride.

To provide acceptable ionic conductivity, ionic salts can be present in amounts from about 0.5 weight percent to about 5 weight percent of the solid state conductive pressure-sensitive adhesive composition. Preferably, ionic salts are present in amounts from about 2 to about 3 weight percent of the solid state conductive pressure-sensitive adhesive composition.

Discontinuous Phase of Domains of Hydrophobic Pressure Sensitive Adhesive

In medical applications, hydrophobic pressure-sensitive adhesive must be tacky at room temperature as well as at skin temperature of patients. Also, the adhesive must be dermatogically acceptable, i.e., after continuous contact with skin, there is little adhesive residue upon removal and there is no significant reaction with skin during adhesion.

The adhesive strength of the discontinuous hydrophobic pressure-sensitive adhesive phase of the composite depends on the type of pressure-sensitive adhesive chosen. The adhesives must provide sufficient adhesive strength to adhere the two-phase composite to the skin of the patient for longer periods of time than provided by ionically-conductive, hydrophilic, solid state, pressure-sensitive adhesives alone.

The hydrophobic pressure-sensitive adhesives can be polymeric adhesive compositions prepared from a combination of monomers, homopolymers, copolymers and tackifiers, or blends thereof to produce polymeric adhesive compositions containing polyacrylates, polyolefins, silicone adhesives, natural or synthetically derived rubber base adhesives, or polyvinyl ethers.

The pressure-sensitive adhesives useful in the composite are hydrophobic in order to resist interaction with the hydrophilic, solid state, pressure-sensitive adhesive continuous phase or with moisture or other body exudate gathering at the skin or skin opening during use. The composite retains its strong adhesiveness even in the presence of water and humectant. Excess moisture is taken away from the skin surface by the continuous phase of ionically-conductive, hydrophilic, solid state, pressure-sensitive adhesive. Preferred adhesives are acrylic pressure-sensitive adhesive copolymers comprising "A" and "B" monomers as follows: Monomer A is a hydrophobic monomeric acrylic or methacrylic acid ester of alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A monomers are n-butyl, n-pentyl, n-hexyl, isoheptyl, n-nonyl, n-decyl, isohexyl, 2-ethyloctyl, isooctyl and 2-ethylhexyl acrylates. The most preferred monomer is isooctyl acrylate.

Monomer B is a reinforcing monomer comprising acrylic acid; methacrylic acid; alkyl acrylates and methacrylates containing 1 to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; N-vinyl-2-pyrrolidone; vinyl ethers such as vinyl tertiary-butyl ether; substituted ethylenes such as derivatives of maleic anhydride, dimethyl itaconate and monoethylformate; or vinyl perfluoro-n-butyrate. The preferred B monomers are acrylic acid, acrylamide and N-vinyl-2-pyrrolidone. The most preferred B monomer is N-vinyl-2-pyrrolidone.

The A monomer in such copolymer is present in the pressure-sensitive adhesive copolymer in an amount by weight of about 85 to 98 percent by weight, and preferably about 90 to 98 percent by weight of the weight of all monomers in the copolymer.

The B monomer in such a copolymer is present in the pressure-sensitive adhesive copolymer in an amount by weight of about 2 to about 15 percent by weight, and preferably about 2 to 10 percent by weight of the weight of all monomers in the copolymer.

In addition to A and B monomers, polystyrene can be added to form a desirable copolymer of isooctyl acrylate/acrylic acid/polystyrene in a weight fraction ratio of 96:2:2 and having an inherent viscosity of 1.35 dl/g.

Most preferably, the pressure-sensitive adhesive of the present invention is an isooctyl acrylate/N-vinyl pyrrolidone copolymer in a weight fraction ratio of 91:9 and having an inherent viscosity of about 1.6 dl/g.

The adhesive copolymers of the above type are known and their method of preparation is well known to those skilled in the art, having been described for example, in U.S. Pat. No. RE 24,906 of Ulrich. Since the pressure-sensitive adhesives described above are inherently rubbery and tacky and are suitably heat and light stable, there is no need to add tackifiers, crosslinkers, or stabilizers. However, such may be added if desired.

The availability and preparation of other pressure-sensitive adhesives useful in the present invention are described in the literature. In the *Handbook of Pressure-Sensitive Adhesive Technology* 2nd Ed., Satas, Editor, (Von Nostrand Reinhold, New York 1989), a number of types of useful pressure-sensitive adhesives are discussed: natural rubber adhesives; A-B-A block copolymers, (such as polystyrene-polybutadiene-polystyrene (S-B-S), polystyrene-polyisoprene-polystyrene (S-I-S), polystyrene-poly(ethylene/butylene)-polystyrene (S-EB-S), and polystyrene-poly(ethylene/propylene)-polystyrene (S-EP-S) polymers); butyl rubbers and polyisobutylene; vinyl ether polymers; silicones; polyisoprene; butadiene acrylonitrile rubber; polychloroprene; atactic polypropylene; and additional descriptions of acrylic adhesives and acrylic dispersions.

Desirably among these available pressure-sensitive adhesives, silicone pressure-sensitive adhesives (such as those disclosed in U.S. Pat. No. 4,039,707) and polystyrene-polyisoprene-polystyrene A-B-A block copolymers (such as those disclosed in U.S. Pat. No. 3,935,338) are useful.

Unexpectedly, hydrophobic pressure sensitive adhesives can be dispersed into the continuous phase of solid state pressure-sensitive adhesive from either water-based latexes or from solvent-based solutions. Thus, the method of preparation of composites of the present invention does not limit the selection of hydrophobic pressure-sensitive adhesives useful in the present invention.

Method of Preparing Two-Phase Composite

The preparation of two-phase composites of the present invention follows processes employed for the formation of hydrophilic, solid state, pressure-sensitive adhesives with the addition of hydrophobic pressure-sensitive adhesive to form a discontinuous phase dispersed therein. Thus, any of the methods of preparation of a solid state conductive pressure-sensitive adhesive composition can be employed if the addition of hydrophobic pressure-sensitive adhesive is not disruptive to the formation of the continuous phase.

Preferably, the two-phase composite is made by mixing an aqueous mixture of the hydrophilic, solid state, pressure-sensitive adhesive with a hydrophobic pressure-sensitive adhesive suspended in an aqueous latex or dissolved in volatile solvent, followed by casting of the composite on a substrate, and drying of water and other volatile solvent to yield a two-phase composite.

Mixture ratios by weight of continuous phase of hydrophilic polymer composition: discontinuous phase of hydrophobic pressure-sensitive adhesive, which include solvent weights, can range of about 196:1 to about 6:1. Preferably, the mixture ratio by weight ranges from about 95:1 to 16:1.

Mixing may be accomplished by using a "Laboratory Dispersator, Series 2000, Model 84" mixer, commercially available from Premier Mill Corporation of Reading, Pa. Mixing processes occur at ambient temperatures and pressures. The mixing should continue until the two phases are intimately interdispersed, regardless of method of alternative preparations described above. Then the mixing is stopped to allow for the removal of any bubbles created during the mixing process.

The composite mixture is spread or coated onto a release liner and volatile solvent is removed. Volatile solvent is removed, generally by application of heat or other drying mechanism. Volatile solvent comprises about 75 weight percent of the hydrophilic polymer composition mixture and about 50 weight percent of the latex mixture containing hydrophobic pressure-sensitive adhesive particles. As drying occurs, the domains of hydrophobic pressure-sensitive adhesive remain dispersed around a continuous phase of hydrophilic, solid state pressure-sensitive adhesive composition. The temperatures of evaporating the volatile solvent(s) without adversely affecting the remaining hydrophobic pressure-sensitive adhesive particles or hydrophilic, solid state, pressure-sensitive adhesive continous phase depends upon the type of volatile solvent(s) employed. Generally, however, the mixture is dried at temperatures between about 50° C. and about 75° C.

As a result, mixture ratios by weight of about 196:1 to 6:1 prior to drying result in a dried composite ratio by weight of continuous phase:discontinuous phase of about 98:1 to 3:1, respectively, when the hydrophobic pressure-sensitive adhesive solids are 50 weight percent of the latex or solution. If the hydrophobic pressure-sensitive adhesive solids are 25 weight percent of the latex or solution, the dried composite ratio by weight can range from about 196:1 to about 6:1. Preferably, the dried composite ratio by weight ranges from about 60:1 to 8:1, and most preferably from about 9:1 to about 21:1.

Films of two-phase composites of the present invention having thicknesses of from about 0.05 mm to about 1 mm, desirably from about 0.07 mm to about 0.38 mm, and preferably from about 0.18 mm to about 0.25 mm. Thereafter, depending on the desired application, the layer of composite may be applied to a backing material by laminating.

For example, a preferred method of preparing a two-phase composite from an essentially non-volatile solid state conductive pressure-sensitive adhesive composition can employ a minimum number of ecologically compatible manufacturing steps. The solvating polymer, ionic salt, and essentially non-volatile plasticizer, if any as needed, are mixed into a solvent which is essentially volatile at or above ambient temperatures, such as water, ethanol, methanol, or isopropanol. To this mixture is added a solution of hydrophobic pressure-sensitive adhesive. A quantity of the resulting mixture of solvating polymer, ionic salt, and any essentially non-volatile plasticizer present in the volatile solvent is then cast onto a surface of a substrate, which can be an inert substrate such as a liner for storage before further processing or a surface of a means for electrical communication having an electrically conductive surface. Then the volatile solvent is essentially evaporated by the application of heat, microwave energy, infrared energy, convective air flow or the like, in order to form the non-volatile solid state conductive pressure-sensitive adhesive continous phase with domains of hydrophobic pressure-sensitive adhesive dispersed therein. Typically, a drying oven heated to about 65° C. can be employed. A product liner can optionally be laminated over the field of the two-phase composite to protect that field from contamination. An extremely thin coating of the two-phase composite can be applied to a substrate surface. Coating thicknesses can range from about 0.125 mm to about 1.25 mm and preferably from about 0.75 mm to about 1 mm, to yield after evaporation of solvent a coating thickness ranging from about 0.05 mm to about 0.38 mm and preferably from about 0.18 mm to about 0.25 mm. With this extremely thin coating on a flexible, electrically conductive substrate, a low profile and conformable biomedical electrode can be made.

Two-phase composites of the present invention can have from about 30 grams/2.54 cm to about 200 grams/2.54 cm adhesion to skin according to the test method identified below. Preferably, skin adhesion can range from about 50 grams/2.54 cm to about 150 grams/cm. Most preferably, skin adhesion can range from about 60 grams/2.54 cm to about 120 grams/2.54 cm.

Two-phase composites of the present invention are translucent or transparent to x-rays, making biomedical electrodes made from such composites suitable for medical procedures where x-ray diagnostic procedures are also employed.

Preparation of Hydrophobic Pressure-sensitive Adhesive

The preparation of hydrophobic pressure-sensitive adhesive useful for forming domains of enhanced adhesiveness depends on the type of adhesive, the type of polymerization (e.g., addition or condensation), and the polymerization technique (e.g., bulk, solution, suspension or emulsion polymerization).

The pressure-sensitive adhesive polymerization technique chosen is selected from conventional polymerization technique(s) known for a particular pressure-sensitive adhesive. Sources of polymerization preparation techniques include *Organic Polymer Chemistry*, K. J. Saunders, Chapman and Hall (Halsted Publishing, New York, 1973), *Applied Polymer Science*, R. W. Tess and G. W. Poehlein, American Chemical Society (American Chemical Society, Washington, D.C., 1981), and *Principles of Polymerization*, George Odien, Wiley-Interscience (John Wiley and Sons, New York, 1981), and the *Handbook of Pressure-sensitive Adhesive Technology*, 2nd Ed., supra.

For example, acrylic pressure-sensitive adhesives may be prepared according to U.S. Pat. No. RE 24,906. When prepared by solution polymerization, the monomers are soluble in solvents, commonly ethyl acetate, cyclohexane, toluene, and n-heptane. The polymer is also usually soluble in the solvent allowing a pure polymer to be coated onto a surface and then dried. When prepared by emulsion polymerization, the latex of water-insoluble polymers in water maintains a phase separation until removal of the water.

Pressure-sensitive adhesives may be prepared by solution polymerization from A-B-A block copolymers, natural rubber, styrene-butadiene, polyisoprene, butyl rubber, polyisobutylene, polychloroprene, and blends thereof. Pellets of the commercially available polymer are mixed into a solvent and heated in the presence of tackifiers and often plasticizers, in order to develop a non-rigid polymer having the requisite tack. Chapters 11, 13, 14, and 19 of the *Handbook of Pressure-sensitive Adhesive Technology* 2nd Ed., referenced above, discusses the choices of materials and methods of preparation. A frequently used tackifier is polyterpene resin.

The rubber based adhesives may also be prepared in a latex. For example, styrene and butadiene may be dispersed in water with an emulsifier (such as sodium alkyl benzene sulfonate) and an initiator (such as potassium persulfate). Polymerization occurs typically anaerobically with mixing for about 16-24 hours at 60° C. Chapter 12 of the *Handbook of Pressure-sensitive Adhesive Technology* 2nd Ed., supra, describes such latex preparation processes.

Silicone pressure-sensitive adhesives are usually commercially supplied in a hydrocarbon solvent. Upon evaporation, the silicones exhibit pressure-sensitive adhesive properties. As described in Chapter 18 of the *Handbook of Pressure-sensitive Adhesive Technology* 2nd Ed., supra, a catalyst (such as an organic peroxide, an amino silane, or a metal salt of an organic acid) is added to reinforce the silicone network, increasing cohesiveness.

The polymerization of vinyl ether homopolymers may be carried out by batch processing, or continuous processing in bulk or in solution. Whichever processing is used, cationic initiators such as $BF_3$ or $AlCl_3$ are present. Copolymers of vinyl ethers and acrylates are polymerized by free radical emulsion polymerization in water with potassium peroxodisulfate. Chapter 17 of the *Handbook of Pressure-sensitive Adhesive Technology* 2nd Ed., supra, describes the polymerization.

If volatile solvents are necessary or desirable for the preparation of the pressure-sensitive adhesive, such solvents can be aliphatic or aromatic hydrocarbons, such as heptane, toluene, xylene, and the like and blends containing other miscible solvents such as ethyl acetate.

Usefulness of the Invention

Biomedical Electrodes

Biomedical electrodes employing two-phase composites of the present invention are useful for diagnostic, therapeutic, electrosurgical, or other medical purposes. In its most basic form, a biomedical electrode comprises a conductive medium contacting mammalian skin and a means for electrical communication interacting between the conductive medium and electrical diagnostic, therapeutic, or electrosurgical equipment.

Among the diagnostic and therapeutic procedures using biomedical electrodes are transcutaneous electronic nerve stimulation (TENS) devices used for pain management, neuromuscular stimulation (NMS) used for treating conditions such as scoliosis, and monitors of electrical output from body functions, such as electrocardiogram (EKG) used for monitoring heart activity and diagnosing heart abnormalities.

Figure 2:
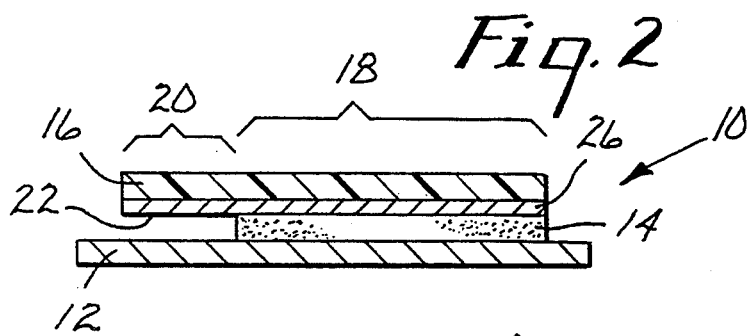
FIG. 2 is a sectional view of the biomedical electrode of FIG. 1.

FIGS. 1 and 2 show either a disposable diagnostic electrocardiogram (EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12.

Electrode 10 includes means for electrical communication 16 comprising a conductor member having a conductive interface portion 18 contacting field 14 of conductive medium and a tab portion 20 not contacting field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical EKG conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred is a polyester film commercially available as "Mellinex" 505-300, 329, 339 film from ICI Americas of Hopewell, Va. coated with a silver/silver chloride ink commercially available as "R-300" ink from Ercon, Inc. of Waltham, Mass. A TENS conductor member 16 can be made of a non-woven web, such as a web of polyester/cellulose fibers commercially available as "Manniweb" web from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Another type of therapeutic procedure, which can employ a biomedical electrode having a two-phase composite of the present invention, is the dispensing of electrical energy to the chest cavity of a mammalian patient to defibrillate abnormal heart beats of the patient. Delivery of a high voltage (e.g., 2000 volts), high current (e.g., 40 amps) electrical charge through one biomedical electrode and receipt of that electrical charge through another biomedical electrode completes the electrical circuit. An example of an electrode useful for defibrillation is disclosed in U.S. Pat. No. 3,998,215 (Anderson et al.), which is incorporated herein by reference.

Another type of therapeutic procedure involving application of electrical current to skin of a patient is iontophoresis, which delivers an iontophoretically active pharmaceutical to or through mammalian skin with aid of an electrical current.

Electrosurgery can use a biomedical electrode using a two-phase composite of the present invention. In this instance, the biomedical electrode serves to receive in a dispersed fashion electrical signals introduced to the patient at an incision site using an electro-surgical cutting electrode. An electro-surgical system usually comprises a generator providing high-frequency alternating current on demand under monitored conditions, the cutting electrode having an extremely high-current density and a flat dispersive biomedical electrode having a very large surface area to provide a low-current density. The dispersive biomedical electrode is placed in intimate and continuous contact with a portion of the mammalian skin which is not subject to the surgical procedure. The alternating current circuit is completed through the body of the patient between the dispersive biomedical electrode and the cutting electrode. Disconnection of the dispersive electrode either from contacting the patient or from the generator could subject the patient to electrical burns where the alternating current circuit leaves the body of the patient.

Figure 3:
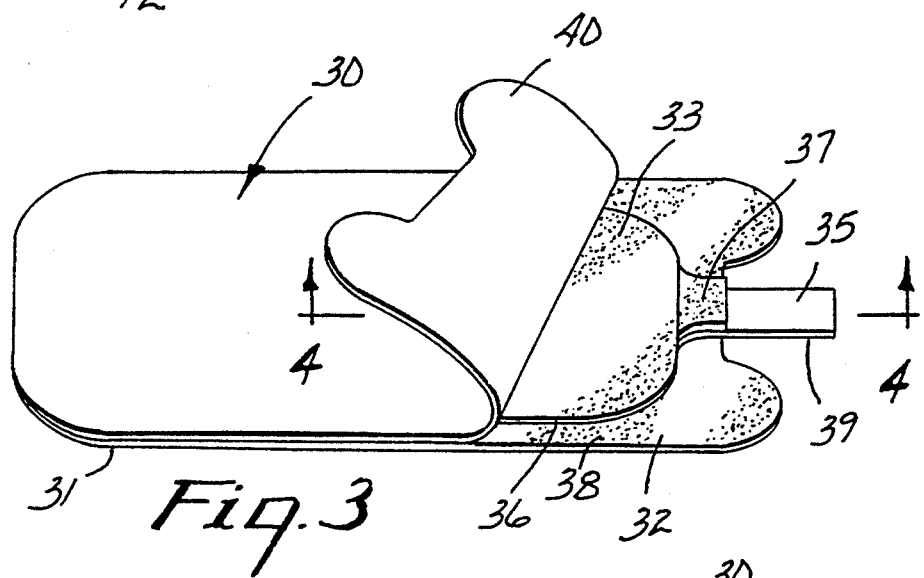
FIG. 3 is a top plan view of a dispersive electrode containing a two-phase composite of the present invention as the conductive medium.
Figure 4:
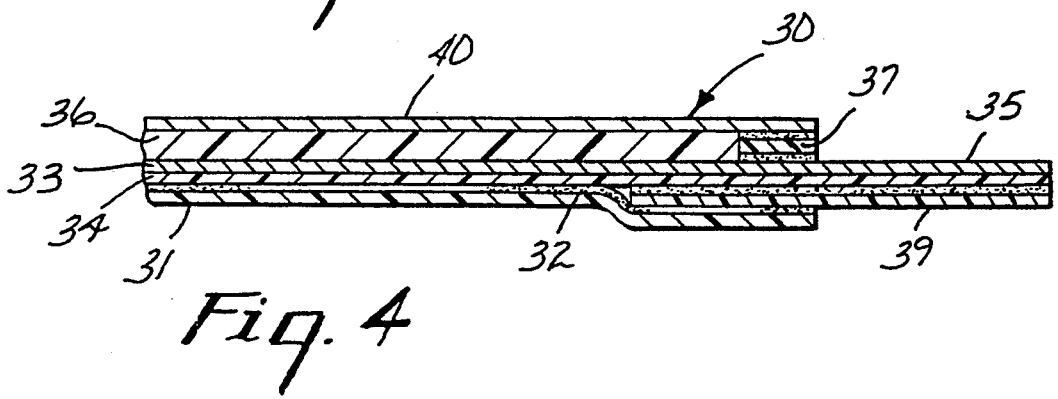
FIG. 4 is a sectional view of the biomedical electrode of FIG. 3.

A dispersive electrode is seen in FIGS. 3 and 4. Dispersive electrode 30 comprises an insulating backing 31 coated on one surface with a biocompatible pressure-sensitive adhesive 32. The backing 31 can be a closed cell polyethylene foam. An electrode plate 33 adheres to a portion of the biocompatible pressure-sensitive adhesive 32. The electrode plate 33 can be an aluminum foil on a conformable polymeric backing 34, e.g., polyester, having aluminum deposited on one surface. The electrode plate 33 has an integrally associated connector tab 35 suited to electrically connect the dispersive electrode 30 to a leadwire which in use is connected to an electrosurgery generator. A field of ionically conductive adhesive 36 of the present invention coats the entire ionically conductive surface of electrode plate 33 except the connector tab 35. An insulating strip 37 double coated with pressure-sensitive adhesive covers that portion of the surface of the connecting tab 35 which underlies the backing 31 and biocompatible pressure-sensitive adhesive 32. The backing 31 and biocompatible pressure-sensitive adhesive 32 have an apron 38 extending beyond the periphery of the electrode plate 33 and electrically-conductive adhesive 36. Apron 38 and insulating strip 37 serve to insulate the electrode plate 33 from direct contact with a patient's skin, thereby avoiding thermal burns and from contact with other conductors (e.g., blood or water) which may result in an electrical short circuit. Supporting connecting tab 35 is a reinforcing layer 39 of nonwoven polyester contacting adhesive 32 and having a single coated adhesive layer contacting tab 35. An optional release liner 40 can be used to protect adhesives 32 and 36 prior to use.

Preferably, to achieve excellent adhesion and low impedance electrical contact with a patient's skin (avoiding hot spots or loss of contract due to motion), surface area of plate 33 and adhesive 36 of the present invention are about 130 cm$^2$. Preferably, the adhesive 36 of the present invention is coated about 0.5 mm thick.

Other examples of biomedical electrodes which can use two-phase composites according to the present invention as conductive adhesive fields include electrodes disclosed in U.S. Pat. Nos. 4,527,087; 4,539,996; 4,554,924; 4,848,353 (all Engel); 4,846,185 (Carim); 4,771,713 (Roberts); 4,715,382 (Strand); 5,012,810 (Strand et al.); co-pending and co-assigned U.S. patent application Ser. No. 07/686,049; co-pending and co-assigned U.S. patent application Ser. No. 07/688,138, the disclosures of which are incorporated by reference herein.

When used for diagnostic EKG procedures, electrodes shown in FIGS. 1 and 2 are preferred. When used for monitoring electrocardiogram (ECG) procedures, electrodes disclosed in U.S. Pat. No. 5,012,810 and application Ser. No. 07/686,049 are preferred. When used for defibrillation procedures or electrosurgical procedures, electrodes shown in FIGS. 3 and 4 or disclosed in U.S. Pat. Nos. 4,539,996 and 4,848,353 are preferred.

In some instances, the means for electrical communication can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto. Further, the means for electrical communication can be a lead wire such as that seen in U.S. Pat. No. 4,771,783. Regardless of the type of means for electrical communication employed, two-phase composites of the present invention can reside as a field of conductive adhesive on a biomedical electrode for diagnostic, therapeutic, or electrosurgical purposes.

Methods of making two-phase pressure-sensitive adhesive composites of the present invention as conductive media for biomedical electrodes include a batch process or in a continuous line process. If prepared by a continuous process, the laminate of a liner, field of two-phase composite of the present invention, and substrate can be wound on a roll for bulk packaging and further processing or can be cut using dies known to those skilled in the art into individual units, such as biomedical electrodes or biomedical electrode subassemblies, for further processing. U.S. Pat. No. 4,795,516 (Strand) and U.S. Pat. No. 4,798,642 (Craighead et al.), which are incorporated by reference herein, disclose processes and equipment useful for a continuous manufacture of biomedical electrodes involving the dispensing of strips of material from rolls and overlaying such strips in a registered continuous manner in order to prepare a strip of electrodes. Further, co-pending, co-assigned U.S. patent application Ser. Nos. 07/686,049 and 07/688,138 disclose methods of preparing biomedical electrode constructions in a continuous strip subassembly.

For example, one method of continuous strip assembly can be the coating of a two-phase composite of the present invention on an electrically conductive surface about 8.9 cm wide, with the coating applied to about the center 5.1 cm section of such width. After evaporation of solvent from the mixture, the coated electrically conductive surface can be bisected along the strip and also cut orthogonally at about 2.54 cm intervals, yielding a number of electrodes 10 seen in FIG. 1 having dimensions of about 2.54 cm $\times$ 4.4 cm with a conductive interface portion 18 of 2.54 cm $\times$ 2.54 cm and a tab portion 20 of 2.54 cm $\times$ 1.9 cm.

As another example, one method of assembly for a dispersive electrode can be the coating of a mixture of two-phase composite of the present invention on a web having an electrically conductive surface about 24 cm wide, with the coating applied to an 18.4 cm section on one side of the web. After evaporation of solvent, the web is then orthogonally cut and laminated to a conformable backing, yielding an electrode seen in FIG. 3 having an overall dimension of 10 cm $\times$ 23 cm.

A further description of the invention may be found in the following examples using the following experimental procedures.

Skin Adhesion Test

Biomedical electrodes were cut to have dimensions of about 2.54 cm $\times$ 4.4 cm with a conductive interface portion of 2.54 cm $\times$ 2.54 cm and a tab portion of 2.54 cm $\times$ 1.9 cm. The electrodes were applied on the backs of human subjects perpendicular to the backbone and rolled with a 2 kg roller to insure uniform application. The electrodes were removed promptly after application from the back using a mechanical pulling device termed an adhesion tester. This device consists of a motor driven screw drive which pulls a 11.4 kg test line to which is attached a metal clip which is 2.54 cm wide. The metal clip is attached to each electrode at its 2.54 cm width during pulling testing. Electrodes were pulled in a plane parallel (180°) to the back and parallel to the long axis of the electrode at a rate of 13-14 cm/min. The adhesion is reported in grams/2.54 cm and based on an average of values from initiation of peel to entire removal of the electrode.

Skin and Back-to-Back Alternating Current Impedance Tests

Skin impedance was measured using a 4800A Vector Impedance Meter manufactured by Hewlett Packard of Palo Alto Calif. on human arms. Biomedical electrodes were placed on the panelists' arms and measured for alternating current impedance in kOhms at a frequency of 10 Hz. Alternating current impedance was measured using an Xtratek ET-65A ECG Electrode Tester from Xtratek Company of Lenexa, Kans. Measurements were conducted in the conventional manner on electrode pairs connected "back-to-back" (adhesive-to-adhesive) using a low level signal suitable for measurements on ECG electrodes. The impedance at 10 Hz was recorded. The Association for the Advancement of Medical Instrumentation (AAMI) has adopted acceptable alternating current impedance at a frequency of 10 Hz to be less than 2000 Ohms for "back-to-back" electrode impedance. Less than about 500 kOhms has been found acceptable for human skin impedance.

EXAMPLES

Example 1—Chemical Crosslinking of PVP

A two-phase composite was prepared in the following manner. Crosslinked polyvinylpyrrolidone (PVP) was prepared according to the procedure of Example 23 of U.S. Pat. No. 4,931,282 (Asmus et al.) using 0.16 weight percent ethylidene-bis-vinylpyrrolidone. The PVP was swollen in water and precipitated by acetone addition to remove residual monomers, dried, and then ground into particles of less than 150 micrometers in diameter. About 9 grams of PVP particles were then swollen in a glycerin (21 grams), water (50 grams), KCl (0.8 grams) solution for 24 hours. To this pressure-sensitive adhesive was added 20 grams of an aqueous base latex of hydrophobic pressure-sensitive adhesive (commercially available as Robond 60 acrylate latex (50 wt. % solids) from Rohm and Haas) by slow addition with stirring and an additional 40 grams of water. The mixture was then stirred mechanically to ensure complete intermixing of the latex into the hydrophilic, solid state, pressure-sensitive adhesive mixture.

The mixture was coated at approximately 0.5 mm onto a backing of polyester having a surface coated with E 1700 silver ink from Ercon, Inc. of Waltham, Mass. thereon. The mixture on the backing was dried in the oven at 93° C. for 2 hours. The final dried conductive medium of two-phase composite was approximately 0.1 mm thick. A release liner was placed on the conductive medium to protect the adhesiveness of the conductive medium.

Skin impedance properties were tested after application to human skin of three individuals. The average skin impedance on three human subjects using a total of 11 samples was 165 kOhms. For all three individuals, the adhesive properties were qualitatively acceptable with good aggressive adhesion, no residue upon removal, and no skin irritation.

Examples 2–20 and Comparison Examples 21 and 22—Irradiation Crosslinking PVP, Formation of Solid State Conductive Pressure-sensitive Adhesive Composition, Formation of Two-Phase Composite, and Preparation and Testing of Biomedical Electrodes Approximately 100 grams of noncrosslinked poly(N-vinyl pyrrolidone) commercially available from BASF of Parsippany, N.J. as solid particles having a size from about 10 micrometers to about 75 micrometers were placed in a resealable plastic bag, purged with nitrogen for 15 minutes, and irradiated with gamma radiation of 155 kGys using a cobalt-60 high energy source to produce crosslinked solid poly(N-vinyl pyrrolidone).

A mixture was prepared in which 33 grams of crosslinked poly(N-vinyl-2-pyrrolidone) homopolymer was added to a solution consisting of 65 grams of polyethylene glycol (400 M.W. from BASF of Parsippany, N.J.), 2 grams potassium chloride and 300 grams of water. The mixture was stirred until equilibrated. To this mixture was blended various hydrophobic pressure-sensitive adhesive formulations in a range of mixture ratios by weight to prepare a variety of two-phase composite examples of the present invention identified in Table 1 for Examples 2 to 20 and Comparison Example 21. Comparison Example 22 was prepared without blending of any hydrophobic pressure-sensitive adhesive formulation into the solid state conductive pressure-sensitive adhesive composition prior to preparing test biomedical electrodes.

To prepare the electrodes, two-phase composite pressure-sensitive adhesive for each Example 2-20 and Comparison Example 21 and solid state pressure-sensitive adhesive for Comparison Example 22 was strip-coated horizontally on the center of a 8.89 cm×17.78 cm polyester backing coated with silver. The silver had a conductance of 0.5 mhos and was 7.62 micrometers thick. Each mixture was coated on an area of 5.08 cm×17.78 cm at approximately 76.2 micrometers thick. Each mixture was dried in an oven at 66° C. for 15–20 minutes. Biomedical electrodes were made by cutting the dried sheet into 2.54 cm×4.2 cm strip consisting of a 2.54×2.54 cm conductive adhesive contacting area and a connecting tab of 2.54×1.6 cm lead wire connection area. DC Offset was measured using an Xtratek ET-65A ECG electrode tester from Xtratek of Lenexa, Kans. to determine if DC offset was within the AAMI standard of less than 100 mvolts throughout the test duration.

TABLE 1

| Example | Hydrophobic PSA | Mixture Ratio (before drying) | Composite Ratio (after drying) | Caliper (mm) | DC Offset (m VOlts) | AC Impedance (Ohms) | Skin Impedance (k Ohms) | Skin Adhesion (grams/2.54 cm) |
|---|---|---|---|---|---|---|---|---|
| 2 | IOA/NVP[1] | 196:1 | 196:1 | 0.18 | 2.2 | 313 | 357 | 38 |
| 3 | IOA/NVP | 95:1 | 95:1 | 0.15 | 0.4 | 440 | 399 | 66 |
| 4 | IOA/NVP | 36:1 | 36:1 | 0.18 | 0 | 420 | 349 | 81 |
| 5 | IOA/NVP | 16:1 | 16:1 | 0.15 | 1.9 | 396 | 366 | 127 |
| 6 | IOA/NVP | 6:1 | 6:1 | 0.20 | 3.0 | 699 | 462 | 182 |
| 7 | IOA/AA/S[2] | 196:1 | 114:1 | 0.18 | 3.9 | 413 | 386 | 44 |
| 8 | IOA/AA/S | 95:1 | 55:1 | 0.18 | 0.4 | 352 | 370 | 48 |
| 9 | IOA/AA/S | 36:1 | 21:1 | 0.20 | 0 | 379 | 358 | 66 |
| 10 | IOA/AA/S | 16:1 | 9:1 | 0.13 | 0.6 | 324 | 330 | 91 |
| 11 | IOA/AA/S | 6:1 | 4:1 | 0.13 | 0.9 | 431 | 366 | 82 |
| 12 | ROBOND[3] | 196:1 | 95:1 | 0.11 | 0.6 | 407 | 360 | 35 |
| 13 | ROBOND | 95:1 | 48:1 | 0.08 | 0.4 | 420 | 380 | 28 |
| 14 | ROBOND | 36:1 | 18:1 | 0.10 | 0.3 | 449 | 416 | 35 |
| 15 | ROBOND | 16:1 | 8:1 | 0.15 | 0.3 | 471 | 482 | 80 |
| 16 | ROBOND | 6:1 | 3:1 | 0.08 | 2.5 | 649 | 470 | 114 |
| 17 | FLEXBOND[4] | 196:1 | 95:1 | 0.10 | 0 | 265 | 310 | 47 |
| 18 | FLEXBOND | 95:1 | 48:1 | 0.10 | 0.2 | 336 | 354 | 49 |
| 19 | FLEXBOND | 36:1 | 18:1 | 0.10 | 1.4 | 432 | 397 | 60 |
| 20 | FLEXBOND | 16:1 | 8:1 | 0.11 | 1.7 | 519 | 400 | 86 |
| 21* | FLEXBOND | 6:1 | 3:1 | 0.13 | 0.5 | 2685 | 396 | 121 |

TABLE 1-continued

| Example | Hydrophobic PSA | Mixture Ratio (before drying) | Composite Ratio (after drying) | Caliper (mm) | DC Offset (m VOlts) | AC Impedance (Ohms) | Skin Impedance (k Ohms) | Skin Adhesion (grams/2.54 cm) |
|---|---|---|---|---|---|---|---|---|
| 22* | NONE | ∞ | ∞ | 0.18 | 2.1 | 341 | 310 | 44 |

[1] Isooctyl acrylate/N-vinyl pyrrolidone copolymer (91:9 weight ratio, inherent viscosity 1.6 dl/g) dispersed at 25% weight solids in a solvent blend of 50/50 heptane/ethyl acetate

[2] Isooctyl acrylate/acrylic acid/polystyrene copolymer 96:2:2 weight ratio inherent viscosity 1.35 dl/g) (M.W. 10,000) syspended at 43 weight percent solids in ethyl acetate

[3] "Robond 60" latex acrylate copolymer dispersed at 50% weight solids in ethyl acetate available from Rohm & Haas (Philadelphia, PA)

[4] "Flexbond 150" latex vinyl acetate dioctyl maleate coploymer dispersed at 50% weight solids in water, commercially available from Air Products & Chemicals Inc. of Allentown, PA

*Comparison Examples

Table 1 shows that skin adhesion can be greatly improved by the mixing of an appropriate amount of a given hydrophobic pressure-sensitive adhesive into a solid state conductive pressure-sensitive adhesive composition. Depending on the amount of skin adhesion desired, the mixture ratio by weight of hydrophilic, solid state, pressure-sensitive adhesive mixture to hydrophobic, pressure-sensitive adhesive can vary from a weight ratio by weight of from about 196:1 to about 6:1 to yield a composite ratio by weight ranging from 196:1 to about 3:1. Only in the instance of Comparison Example 21 did a two-phase composite formulation yield an unacceptable AC impedance according to AAMI standards. In the case of preferred examples 2–6, each mixture ratio by weight produced upon drying a two-phase composite having a composite ratio by weight of value identical to the mixture ratio, because both the solid state pressure-sensitive adhesive and the IOA/NVP copolymer were dispersed in liquids at 25 weight percent solids. Comparing Examples 4 and 22, it is seen that as little as 0.02 weight percent of hydrophobic pressure-sensitive adhesive in the dried two-phase composite nearly doubles skin adhesion without adversely affecting either AC impedance or skin impedance. Similar favorable comparisons can be made between the results of Examples 9, 10, 11, 15, 19, and 20 with Comparison Example 22.

The present invention is not limited to the above embodiments. For an appreciation of the scope of the present invention, the claims follow.

What is claimed is:

1. A two-phase composite of ionically-conductive, pressure-sensitive adhesive, comprising:
a continuous phase of hydrophilic, solid state pressure-sensitive adhesive composition ionically-conductive without the requirement of water being present in the composition, and a discontinuous phase of domains of hydrophobic, pressure-sensitive adhesive composition dispersed in the continuous phase to enhance pressure-sensitive adhesive properties for contacting mammalian skin while maintaining acceptable alternating current impedance;
wherein the continuous phase and the discontinuous phase have a composite ratio by weight of from about 196:1 to about 3:1 continuous phase:discontinuous phase;
wherein the continuous phase of hydrophilic, solid state pressure-sensitive adhesive composition comprises:
(a) from 5 to 50 weight percent of a polymer electrolyte complex, and
(b) from 50 to 95 weight percent of an essentially non-volatile plasticizer present to form a cohesive, pliable, pressure-sensitive adhesive;
said polymer electrolyte complex comprising a solid solution of from 0.5 to 5 weight percent of an ionic salt dissolved in a solvating polymer and ionically conductive without the requirement of water;
said solvating polymer being selected from the group consisting of crosslinked poly(N-vinyl lactam); crosslinked polyacrylamide and its ionic forms; crosslinked polyacrylic acid and its salts; crosslinked poly(2-acrylamide-2-methylpropane sulfonic acid), its salts, crosslinked copolymers of the acid, crosslinked copolymers of salts of the acid, or mixtures thereof, or combinations thereof; and
wherein the discontinous phase of domains of hydrophobic pressure sensitive adhesive composition is selected from the group consisting of polyacrylates, polyolefins, silicone adhesives, natural or synthetically derived rubber base adhesives, and polyvinyl ethers or blends thereof.

2. The two-phase composite according to claim 1, wherein said solvating polymer is selected from the group consisting of crosslinked polyacrylamide and its ionic forms; crosslinked polyacrylic acid and its salts; crosslinked poly(2-acrylamide-2-methylpropane sulfonic acid), its salts, crosslinked copolymers of the acid, crosslinked copolymers of salts of the acid, or mixtures thereof; or combinations thereof; and wherein the plasticizer is present in an amount of from about 65 to about 95 weight percent of the solid state pressure-sensitive adhesive composition to form a cohesive, pliable and pressure-sensitive adhesive composition.

3. The two-phase composite according to claim 1, wherein said solvating polymer is crosslinked poly(N-vinyl lactam) present in an amount of from about 5 to about 50 weight percent of the solid state pressure-sensitive adhesive composition and wherein said plasticizer is present in an amount of from about 50 to about 75 weight percent of the composition.

4. The two-phase composite according to claim 3, wherein said poly(N-vinyl lactam) is crosslinked poly(N-vinyl pyrrolidone) present in an amount of from about 20 to about 45 weight percent of the solid state pressure-sensitive adhesive composition.

5. The two-phase composite according to claim 4, wherein said polyhydric alcohol comprises glycerin, polyethylene glycol (200–600 M.W.) thereof.

6. The two-phase composite according to claim 4, wherein said ionic salt comprises lithium chloride, lithium perchlorate, sodium citrate, potassium chloride, or mixtures thereof.

7. The two-phase composite according to claim 6, wherein said ionic salt is potassium chloride present in an amount of from about 2 to about 3 weight percent of the composition.

8. The two-phase composite according to claim 7, wherein said polyhydric alcohol is polyethylene glycol (200–600 M.W.) present in an amount of about 65 weight percent of the solid state pressure-sensitive adhesive composition.

9. The two-phase composite according to claim 1, further comprising an iontophoretically active pharmaceutical associated with the composite.

10. The two-phase composite according to claim 1, wherein said pressure sensitive adhesive composition is an acrylic copolymer comprising:
 at least one monomer of an acrylic or methacrylic acid ester of an alkyl alcohol wherein said alkyl alcohol contains from 4 to 10 carbon atoms; and
 at least one other monomer selected from the group consisting of acrylic acid, methacrylic acid, alkyl acrylates and methacrylates containing 1 to 3 carbon atoms in said alkyl group; acrylamide; methacrylamide; alkyl-substituted acrylamides containing 1 to 4 carbon atoms in said alkyl substituted group; diacetone acrylamide; N-vinyl-2-pyrrolidone; and vinyl perfluoro-n-butyrate;
 wherein said first monomer has a weight percent of from about 85 percent to about 98 percent and said other monomer has a weight percent of from about 2 percent to about 15 percent.

11. A two-phase composite according to claim 10, wherein said acrylic copolymer comprises isooctyl acrylate/N-vinyl-2-pyrrolidone copolymer.

12. The two-phase composite according to claim 11, wherein the continuous phase and the discontinuous phase have a composite weight ratio of from about 60:1 to about 8:1.

13. The two-phase composite according to claim 11, wherein the continuous phase and the discontinuous phase have a composite ratio by weight of from about 21:1 to about 9:1.

14. A biomedical electrode, comprising:
 (a) a conductive medium comprising a two-phase composite of claim 1; and
 (b) means for electrical communication interacting between said conductive medium and electrical diagnostic, therapeutic, or electrosurgical equipment.

15. The biomedical electrode according to claim 14, wherein said electrical communication means comprises a conductor member having a conductive interface portion contacting said conductive medium and a tab portion not contacting said conductive medium.

16. The biomedical electrode according to claim 14, wherein said electrical communications means comprises a conductor member having an eyelet or snap connector contacting the conductive medium.

17. The biomedical electrode according to claim 14, wherein said solvating polymer is selected from the group consisting of crosslinked polyacrylamide and its ionic forms; crosslinked polyacrylic acid and its salts; crosslinked poly(2-acrylamide-2-methylpropane sulfonic acid), its salts, crosslinked copolymers of the acid, crosslinked copolymers of salts of the acid, or mixtures thereof; or combinations thereof; and wherein the plasticizer is present in an amount of from about 65 to about 95 weight percent of the solid state pressure-sensitive adhesive composition to form a cohesive, pliable and pressure-sensitive adhesive composition.

18. The biomedical electrode according to claim 17, wherein said solvating polymer is crosslinked poly(N-vinyl lactam) present in an amount of from about 5 to about 50 weight percent of the solid state pressure-sensitive adhesive composition and wherein said plasticizer is present in an amount of from about 50 to about 75 weight percent of the composition.

19. The biomedical electrode according to claim 18, wherein said poly(N-vinyl lactam) is crosslinked poly(N-vinyl pyrrolidone) present in an amount of from about 20 to about 45 weight percent of the solid state pressure-sensitive adhesive composition.

20. The biomedical electrode according to claim 19, wherein said polyhydric alcohol comprises glycerin, polyethylene glycol (200–600 M.W.), or mixtures thereof.

21. The biomedical electrode according to claim 19, wherein said ionic salt comprises lithium chloride, lithium perchlorate, sodium citrate, potassium chloride, or mixtures thereof.

22. The biomedical electrode according to claim 21, wherein said ionic salt is potassium chloride present in an amount of from about 2 to about 3 weight percent of the composition.

23. The biomedical electrode according to claim 22, wherein said polyhydric alcohol is polyethylene glycol present in an amount of about 65 weight percent of the solid state pressure-sensitive adhesive composition.

24. The biomedical electrode according to claim 14, further comprising an iontophoretically active pharmaceutical associated with the conductive medium.

25. The biomedical electrode according to claim 14, wherein said pressure sensitive adhesive composition is an acrylic copolymer comprising:
 at least one monomer of an acrylic or methacrylic acid ester of an alkyl alcohol wherein said alkyl alcohol contains from 4 to 10 carbon atoms; and
 at least one other monomer selected from the group consisting of acrylic acid, methacrylic acid, alkyl acrylates and methacrylates containing 1 to 3 carbon atoms in said alkyl group; acrylamide; methacrylamide; alkyl-substituted acrylamides containing 1 to 4 carbon atoms in said alkyl substituted group; diacetone acrylamide; N-vinyl-2-pyrrolidone; and vinyl perfluoro-n-butyrate;
 wherein said first monomer has a weight percent of from about 85 percent to about 98 percent and said other monomer has a weight percent of from about 2 percent to about 15 percent.

26. A biomedical electrode according to claim 25, wherein said acrylic copolymer comprises isooctyl acrylate/N-vinyl-2-pyrrolidone copolymer.

27. The biomedical electrode according to claim 14, wherein the continuous phase and the discontinuous phase have a composite ratio by weight of from about 60:1 to about 8:1.

28. The biomedical electrode according to claim 27, wherein the continuous phase and the discontinuous phase have a composite ratio by weight of from about 21:1 to about 9:1.

29. A method of preparing a two-phase composite according to claim 1, comprising the steps of:
 (a) mixing solvating polymer, ionic salt, and an amount of essentially non-volatile plasticizer sufficient to form a cohesive, hydrophilic solid state pressure-sensitive adhesive, into a solvent which is essentially volatile above ambient temperatures to form a first suspension or solution;

(b) mixing a latex or solution of hydrophobic pressure-sensitive adhesive into the first suspension or solution in a mixture ratio by weight of from about 196:1 to about 6:1 of first suspension or solution:-latex or solution to form a combined mixture;
(c) casting the combined mixture onto a substrate; and
(d) removing the solvent to form a two-phase composite according to claim 1.

30. The method according to claim 29, wherein said substrate has an electrically conductive surface and wherein a biomedical electrode is formed from said two-phase composite on said surface.

* * * * *

UNITED STATES PATENT AND TRADEMARK OFFICE
CERTIFICATE OF CORRECTION

PATENT NO.: 5,338,490

DATED: August 16, 1994

INVENTOR(S): Dietz et al.

It is certified that error appears in the above-identified patent and that said Letters Patent is hereby corrected as shown below:

At columns 17 and 18, Table 1, the heading at the top of the table under DC Offset, "(mVOlts)" should read --(m Volts) --.

At columns 19 and 20, Table 1, the heading at the top of the table under DC Offset, "(mVOlts)" should read --(m Volts) --.

At columns 19 and 20, Table 1, footnote 3, after "in", delete "ethyl acetate", insert --water, commercially--.

At column 22, line 1, "according to Claim 17" should read -- according to Claim 14--.

At column 22, line 25, "according to Claim 22" should read -- according to Claim 20--.

Signed and Sealed this

Ninth Day of January, 1996

Attest:

BRUCE LEHMAN

Attesting Officer

Commissioner of Patents and Trademarks